(12) United States Patent
Oglesby

(10) Patent No.: US 8,474,529 B2
(45) Date of Patent: Jul. 2, 2013

(54) CONTROL OF CONCENTRIC TUBING DIRECTION

(75) Inventor: Kenneth Doyle Oglesby, Tulsa, OK (US)

(73) Assignee: Regency Technologies LLC, Tulsa, OK (US)

( * ) Notice: Subject to any disclaimer, the term of this patent is extended or adjusted under 35 U.S.C. 154(b) by 351 days.

(21) Appl. No.: 12/754,139

(22) Filed: Apr. 5, 2010

(65) Prior Publication Data

US 2010/0258322 A1 Oct. 14, 2010

Related U.S. Application Data

(60) Provisional application No. 61/167,939, filed on Apr. 9, 2009.

(51) Int. Cl.
*E21B 47/00* (2012.01)
(52) U.S. Cl.
USPC ........................................ 166/255.2
(58) Field of Classification Search
USPC ........................ 166/255.2; 138/114
See application file for complete search history.

(56) References Cited

U.S. PATENT DOCUMENTS

| | | | | |
|---|---|---|---|---|
| 2,165,426 A | * | 7/1939 | Tuttle et al. | 248/188.5 |
| 2,800,987 A | * | 7/1957 | Potts | 192/45.005 |
| 4,738,512 A | * | 4/1988 | Faatz et al. | 359/811 |
| 5,269,377 A | | 12/1993 | Martin | |
| 5,435,351 A | | 7/1995 | Head | |
| 5,685,237 A | * | 11/1997 | Lehrman | 108/118 |
| 5,821,452 A | | 10/1998 | Neuroth et al. | |
| 6,015,015 A | | 1/2000 | Luft et al. | |
| 6,116,340 A | | 9/2000 | Wilson et al. | |
| 6,122,115 A | * | 9/2000 | Plummer et al. | 359/822 |
| 7,775,303 B2 | * | 8/2010 | Goting | 175/389 |
| 2005/0189146 A1 | * | 9/2005 | Oglesby | 175/107 |

OTHER PUBLICATIONS

An Introduction to Coiled Tubing: History, Application, and Benefits, International Coiled Tubing Association.

* cited by examiner

*Primary Examiner* — Giovanna Wright
*Assistant Examiner* — Kipp Wallace
(74) *Attorney, Agent, or Firm* — Head, Johnson & Kachigian, P.C.

(57) ABSTRACT

An apparatus and a method to control rotational positioning of continuous concentric tubing that extends from a surface downhole in a subterranean well or bore. In one version, a continuous cylindrical inner tube resides within and is concentric with a cylindrical outer tube. At least one elliptical lobe extends from the continuous inner tube. The invention utilizes diameter restrictions within and attached to the outer concentric tubing so that the elliptical lobe or lobes engage the diameter restrictions. Accordingly, rotation of one tube rotates or orients the other tube.

16 Claims, 2 Drawing Sheets

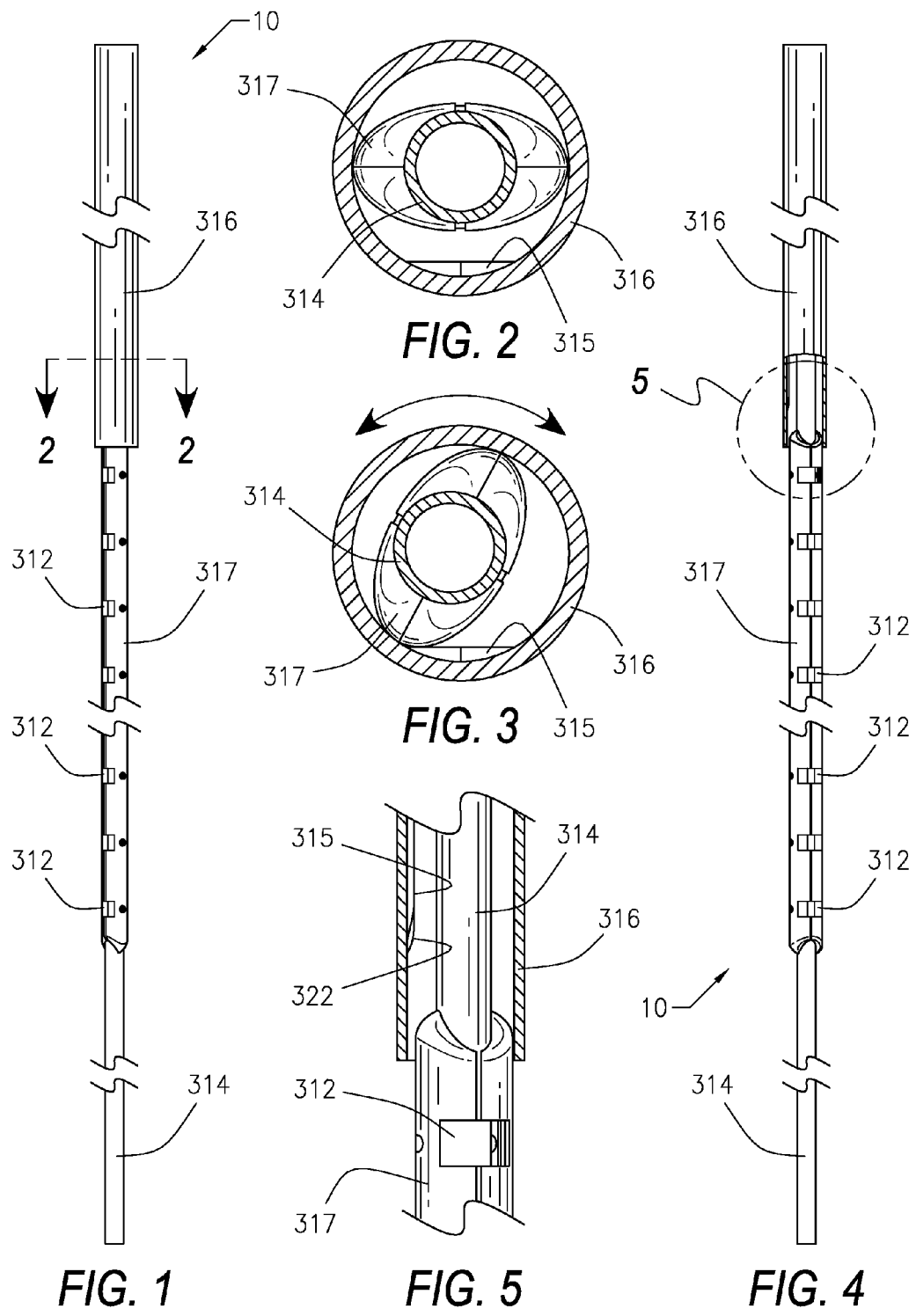

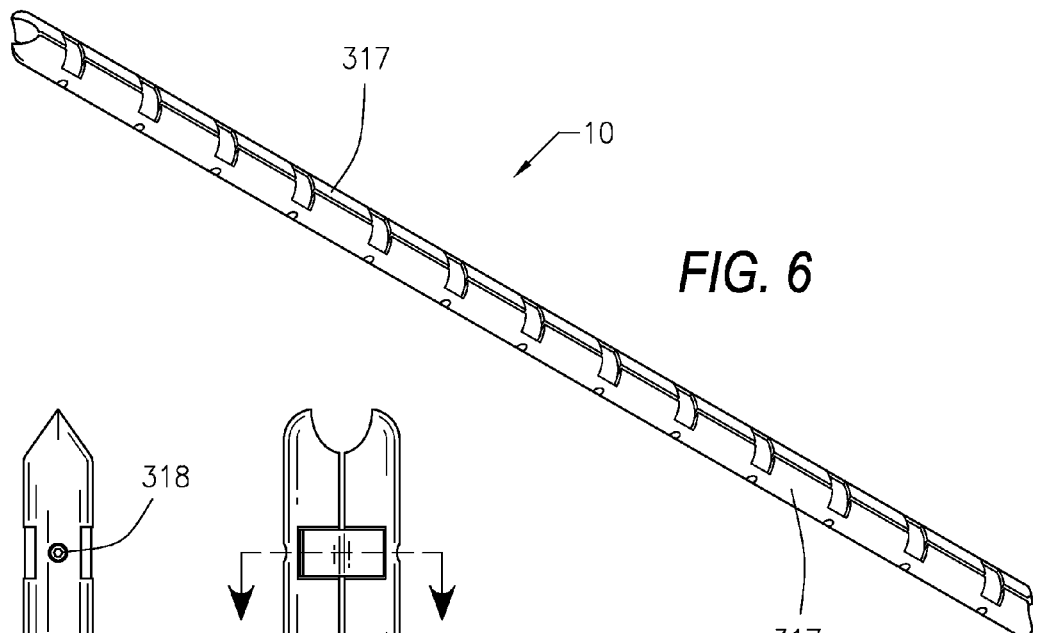
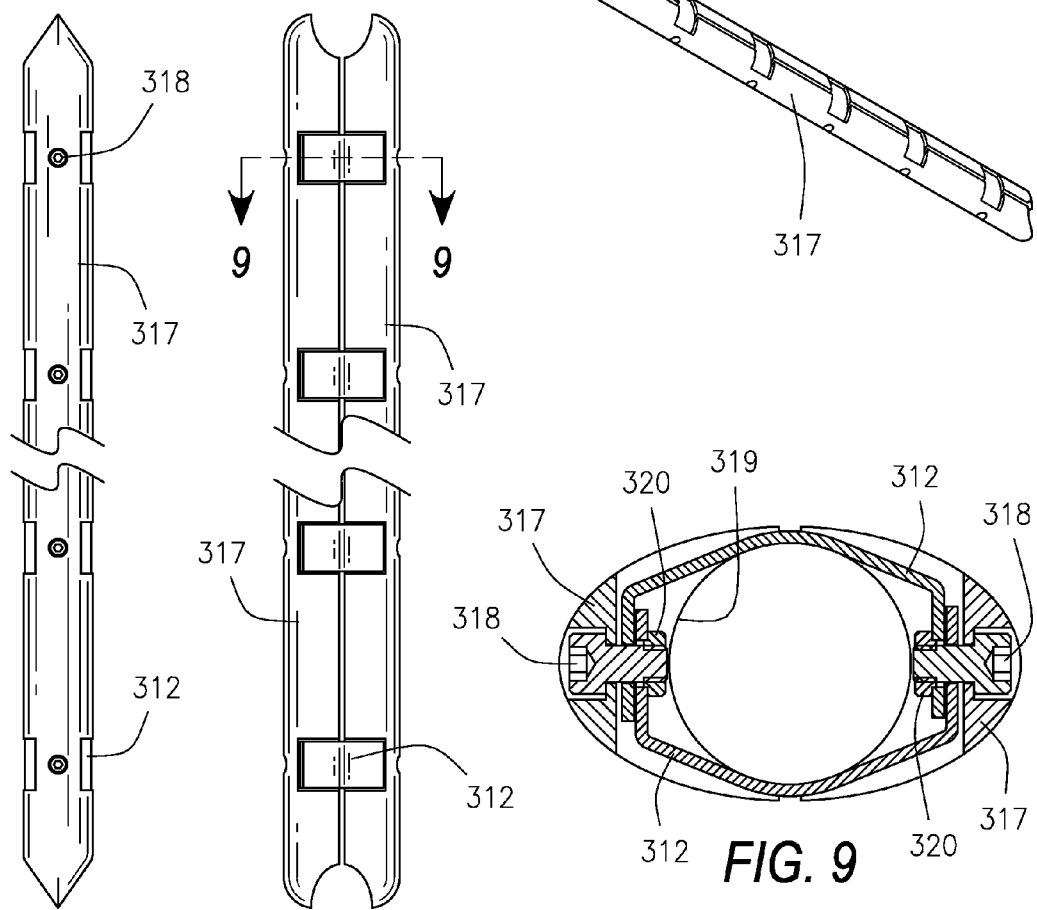

CONTROL OF CONCENTRIC TUBING DIRECTION

CROSS-REFERENCE

This application claims priority to U.S. Provisional Patent Application Ser. No. 61/167,939, filed Apr. 9, 2009, incorporated in its entirety herein by reference.

BACKGROUND OF THE INVENTION

1. Field of the Invention

The present invention relates to an apparatus and to a method to at least partially rotate continuous tubing in order to control rotational positioning of concentric tubing.

2. Prior Art

The oil and gas drilling, production, and service industries often make use of tubing in a concentric configuration with a first tube inside of a larger tube. In the past, downhole tubing was typically assembled from a series of lengths or sections, commonly called "joints," joined together at the ends. The sections would be connected on installation downhole and then unconnected on retrieval. More recently, continuous tubing has been introduced. Continuous tubing may be fabricated from carbon steel or other material. The continuous tubing may be manufactured in a number of ways including by welding a continuous flat strip into a tube. The tubing diameter typically ranges from less than an inch up to four inches. Tube lengths in excess of 30,000 feet have been manufactured.

Coiled tubing and its associated equipment provide a relatively small foot print and short rig-up and rig-down times. In addition, it provides for faster movement in and out of the well, called "trips."

The continuous length of concentric tubing is stored wound on a spool or reel. The concentric tubing is later straightened prior to entering the well bore. In order to install, the larger diameter tubing is installed or run down in the bore from the surface downhole. Thereafter, the inner tubing is installed or run down inside and concentric to the larger diameter outer tubing.

Rotation and partial turning of such tubing is often required during drilling, during oil or gas production or during service operations. Rotation or turning the tubing that extends down in a vertical, directional, or horizontal well or bore has heretofor been accomplished by either turning the tubing at the surface or by utilizing a downhole motor.

If the tubing is coiled or continuous tubing on a spool, it cannot be easily rotated or turned from the surface without rotating the entire spool. In these situations, a downhole motor may be required.

The present invention has many applications. Turning or orienting such a tube downhole is important when the tubing or tube is connected to a tool in a bore downhole in the earth, such as for a drill bit on the end of the tubing, and that tool needs to be turned or partially rotated. Another example is when a tool needs to be oriented in a particular direction, such as for control of a downhole directional instrument or tool, such as a "whipstock."

Also, a short rotation of the coiled tube combined with a vertical, axial movement allows attachment, release and/ or sealing of a separate tube or tool. One type of tool is commonly known as a "J" slot type connection, which is well known in the industry. In particular, directional or horizontal drilling requires such specific movement of downhole tools. Such downhole tools can be drill bits, and drill motors attached to directional kick-off tools, bent pipe, measurement instruments, or even a given orientation line on the downhole tubing.

Continuous coiled tubing is spooled and re-spooled on to a reel. Continuous coiled tubing is normally stored on a reel or spool for transportation and storage at the surface. In order to install, the tubing is unwound off of a reel at the surface and passed over a guide arch or gooseneck their straightened and then directed downhole. An injector head provides the motive force to run the tubing downhole. The reverse operation is performed to retrieve the tubing.

The present invention, thus, also provides a means or mechanism for rotating, turning or orienting the tubing that may be helpful in spreading out the stresses encountered in the multiple uncoiling and recoiling processes, thereby extending the useful life of the continuous tubing.

SUMMARY OF THE INVENTION

To address these needs which arise from the use of concentric tubing, the present invention proposes to rotate, turn, or partially turn, rotate or orient an affected tube that is attached to a tool by rotation of a second concentric tubing or control tube. One tube is of the continuous or coiled type.

In one non-limiting application, a tool is attached at the end of the affected tube downhole. When one of the concentric tubes is rotated or turned, the other concentric tube will be rotated and any attached tool will, thus, be turned.

In one preferred embodiment, the inner affected tube will have a lobe or lobes attached in either a temporary or permanent manner by strap, clamp, welding or otherwise to its outside diameter or by connection to a tool joint or threaded "sub" or short joint. The outer concentric control tube will have at least one rotation restriction such as a lobe or flat spot in its inner diameter.

The instant invention can be employed downhole, in the well bore or on the surface. The present invention can be utilized on the earth's surface to turn or orient coiled tubing while being spooled out or re-spooled. This would allow different stress points to be encountered during the re-spooling process which may he important for the useful life of the coiled tubing.

In another embodiment, the invention can be installed in conjunction with one or more swivels on the control tubing (not shown) at either end of the tubing, but typically only one at the surface. Swivels need not interfere with the internal diameter of the control tube and thus do not interfere with the operation of the proposed invention. Swivels are known load (axial or journal) bearing tools that allow rotational movement of the control tube, but are fixed to prevent vertical movement. Thus, swivels can support the weight of the control tube string, if supported on the other side by another large casing or tube or the drill rig, itself. An example of a surface positioned, non-sealing, weight supporting rotating swivel is the combination of the slips and drill table on the drilling rig. Down in the well and at the deepest end of the control tube, a swivel can be in conjunction with a downhole tool, such as a whipstock, to allow for rotational movement of the control tube without needlessly moving the downhole tool.

In another embodiment, the control tube can be independent or free at the bottom and connected to a rotatable slip assembly at the surface that will allow rotation of that tube. The indirectly rotated tube does not need a swivel as it must be movable vertically.

Either the inner or outer concentric tube can be coupled to various mechanisms in order to rotate, partially rotate, or orient the affected tube.

The mechanisms to rotate the control tube, the inner tube, or the outer tube can include, without limitation, manual operation by a pipe wrench, crescent wrench, clamps with a bar, or other manual means. Other mechanisms to rotate can include automatic means which are gear driven by electric, pneumatic, or hydraulic motors. One example of a conventional mechanism to rotate the control tube is by a rotary table of a drilling rig.

BRIEF DESCRIPTION OF THE DRAWINGS

FIG. 1 is a partially exploded view of an assembly of the present invention to control rotational positioning of a concentric continuous tube;

FIGS. 2 and 3 illustrate sectional views showing alternate positions of the assembly taken along section line 2-2 of FIG. 1;

FIG. 4 is a partially exploded view of the present invention shown in FIG. 1;

FIG. 5 is an enlarged sectional view taken along section line 5-5 of FIG. 4;

FIGS. 6, 7 and 8 illustrate alternate views of lobes of the assembly of the present invention; and FIG. 9 is a sectional view taken along section 9-9 of FIG. 8.

DETAILED DESCRIPTION OF THE PREFERRED EMBODIMENTS

The embodiments discussed herein are merely illustrative of specific manners in which to make and use the invention and are not to be interpreted as limiting the scope of the instant invention.

While the invention has been described with a certain degree of particularity, it is to be noted that many modifications may be made in the details of the invention's construction and the arrangement of its components without departing from the spirit and scope of this disclosure. It is understood that the invention is not limited to the embodiments set forth herein for purposes of exemplification.

Continuous tubing is jointless steel or composite tubing that is spooled onto a reel or coil for transportation, storage, and deployment. It can be deployed or installed inside and concentric to a larger diameter tube.

FIG. 1 shows an exploded plan view of an overall assembly of one possible version of an assembly 10 to control rotational positioning of a continuous tube. A continuous inner tube 314 is surrounded by a larger diameter outer tube 316. FIGS. 2 and 3 illustrate sectional views showing alternate positions taken along section line 2-2 of FIG. 1. A first cylindrical outer tube 316 has a diameter restriction 315 at its inner diameter and is attached to its inner surface. The diameter restriction 315 may be integral with the outer tube 316 or may be secured to the outer tube 316 by periodic tack welding, by fasteners passing through the outer tube 316, or by another mechanism.

A cylindrical inner tube 314 is mostly concentric with and has a smaller diameter than the outer tube 316 and resides therein. A pair of opposed elliptical lobe halves 317 surround the inner tube 314 within the outer tube 316. The two lobe halves 317 are attached to the inner tube 314 with a series of clamps 312.

Rotation of the outer tube 316 causes the diameter restriction 315 to rotate and engage the lobes 317. Once the lobes engage the diameter restriction, the diameter restriction 315 forces the inner tubing 314 with the lobes 317 to rotate or turn with the outer tube 316.

FIGS. 4 and 5 illustrate the assembly 10 with portions cut-away for clarity. The lobes 317 surround the inner tubing 314 and both of the lobes reside within the outer tube 316.

FIGS. 6, 7 and 8 illustrate alternate views of the lobes 317 of the present invention. FIG. 9 is a detailed view of the double lobe attachment made up of two lobe halves 317 held together by clamps 312 and fasteners, such as bolts 318 tightening the clamps onto the inner tubing (not shown in FIGS. 6 through 9).

The inner surface of the lobes 317 may optionally have linear grooves or roughened surfaces 319 to discourage or prevent slipping on the outer surface of the inner tube 314.

FIG. 5 shows one preferred arrangement with the mostly concentric inner tube 314 as the affected tube having two restrictive lobes 317 of some length that are attached by clamps or other means to the inner tube. A diameter restriction 315 has a top guide 322 which provides a ramped surface installed on the inner surface of outer concentric tube 316. Guide 322 on diameter restriction 315 ensure that lobes 317 on the inner string moves to either side of the restriction 315 for further vertical movement of the inner string. A similar guide on the end of lobe 317 is also required to facilitate this desired movement.

The outer tube 316 can be free standing on the bottom and top or attached to a swivel (not shown) or some other device allowing rotation (free or limited). When the outer tube 316 is sufficiently rotated, the inner tube 314 will be rotated.

The number of lobes 317 on the inner concentric tube 314 can be one, two, three or more, but would be reasonably limited. They may be temporarily attached by clamps 312 (or bolts or straps—not shown) or permanently attached by welding. They may be permanent threaded subs or threaded connections on the inner tube 314 as well. The length of either the lobes 317 or the restriction 315 can be short, but the other must be as long as the control time or length is required.

The outer tube 316 has one or more lobes 315, diameter reducers that are temporarily or permanently attached by welds or fastener, such as screws/ bolts or threaded connections to its inner diameter.

Alternately, two barriers can be installed and attached to the inside of the continuous outer tube 316 which will accomplish the same function but require less rotation to affect the continuous inner tube.

In ordinary operation, continuous tubing cannot rotate downhole unless the full string and the surface coil or reel is rotated. Alternatively, a downhole motor on the end of the continuous tubing can rotate a downhole tool, such as a drill bit or orient a downhole tool, but this is expensive and requires larger diameter sizes.

One particular use of the instant invention is for directional control of an oil and gas drilling process when continuous tubing is utilized.

If a short pipe section is bent and installed between the continuous tubing (from the surface down to some depth) and a downhole motor with a drill bit attached to the motor, then a directional hole can be drilled.

In accordance with the present invention, if lobes are installed on the continuous inner tubing and run inside of an outer tubing of jointed pipe with a diameter restriction of the present invention, then rotation of the outer tubing will rotate or orient the inner continuous concentric tubing 314. Thus, if a change in drilling direction of the drill bit is desired, the outer concentric tubing is turned in the desired direction which turns the inner concentric string which turns the bent sub in the favorable desired direction. With the bent sub turned, the motor and the bit will follow into the favorable direction desired. In such directional drilling applications, only rotations of the bent sub/bit of about 10-20 degrees in either direction is sufficient in most cases.

While one or more embodiment of this invention have been illustrated in the accompanying drawings and described above, it will be evident to those skilled in the art that changes and modifications may be made therein without departing from the essence of this invention. All such modifications or variations are believed to be within the sphere and scope of the invention as defined by the claims appended hereto.

Whereas, the present invention has been described in relation to the drawings attached hereto, it should be understood that other and further modifications, apart from those shown or suggested herein, may be made within the spirit and scope of this invention.

What is claimed is:

1. An apparatus for rotating a continuous tube that extends from a surface down in a subterranean well or bore comprising:
    at least one continuous cylindrical inner tube extending down in a subterranean well or bore;
    at least one concentric continuous cylindrical outer tube extending down in a subterranean well or bore having a larger diameter than said inner tube so that said outer tube surrounds said inner tube and is spaced therefrom;
    at least one elliptical lobe extending from an outer surface of said inner tube; and
    at least one diameter restriction on an inner surface of said outer tube in order to engage said elliptical lobe upon rotation of one of said tubes, wherein said inner tube and said at least one elliptical lobe move axially with respect to said outer tube during said rotation.

2. An apparatus for rotating tubing as set forth in claim 1 wherein said at least one diameter restriction includes a plurality of diameter restrictions spaced periodically along said inner surface of said outer tube.

3. An apparatus for rotating tubing as set forth in claim 1 wherein said at least one diameter restriction is welded to said inner surface of said outer tube.

4. An apparatus for rotating tubing as set forth in claim 1 wherein said at least one diameter restriction is connected to said inner surface by fasteners passing through said outer tube.

5. An apparatus for rotating tubing as set forth in claim 1 wherein each said at least one elliptical lobe is composed of two opposed halves.

6. An apparatus for rotating tubing as set forth in claim 5 wherein said two halves of said elliptical lobe are secured to said inner tube by a plurality of clamps.

7. An apparatus for rotating tubing as set forth in claim 1 wherein said at least one elliptical lobe includes a roughened or grooved surface to mate with said outer surface of said inner tube.

8. A method to control rotational positioning of a continuous tube extending from a surface to downhole, which method comprises:
    rotating a first continuous cylindrical outer tubing having at least one diameter restriction on an inner surface of said first outer tubing;
    providing at least one elliptical lobe extending from a concentric continuous cylindrical inner tubing within said first outer tubing;
    engaging said diameter restriction with said at least one elliptical lobe in order to rotate said inner tubing; and
    moving said at least one elliptical lobe and said inner tube axially with respect to said outer tube while performing the foregoing steps.

9. A method to control rotational positioning as set forth in claim 8 wherein each said elliptical lobe is composed of two halves.

10. A method to control rotational positioning as set forth in claim 9 including connecting said two halves of said elliptical lobe with said inner tube with a plurality of clamps.

11. A method to control rotational positioning as set forth in claim 8 including spacing a plurality of diameter restrictions periodically along said inner surface of said outer tube.

12. A method to control rotational positioning of a tube extending from a surface downhole, which method comprises:
    providing a continuous first cylindrical outer tubing extending down in a subterranean well or bore having at least one diameter restriction on an inner surface thereof;
    providing a continuous concentric inner tubing extending down in a subterranean well or bore having a smaller diameter than said outer tubing;
    providing at least one elliptical lobe-extending from said concentric cylindrical inner tubing;
    rotating said inner tubing to engage said at least one elliptical lobe with said at least one diameter restriction; and
    moving said at least one elliptical lobe and said inner tube axially with respect to said outer tube while performing the forgoing steps.

13. A method to control rotational positioning of a concentric tube as set forth in claim 12 wherein said elliptical lobe is composed of two halves.

14. A method to control rotational positioning of a concentric tube as set forth in claim 12 including connecting said two halves of said elliptical lobe-with said inner tube with a plurality of clamps.

15. A method to control rotational positioning as set forth in claim 12 including spacing a plurality of said diameter restrictions periodically along said inner surface of said outer tube.

16. An apparatus for rotating a continuous tube that extends from a surface down in a subterranean well or bore comprising:
    at least one continuous cylindrical inner tube extending down in a subterranean well or bore;
    at least one concentric continuous cylindrical outer tube extending down in a subterranean well or bore having a larger diameter than said inner tube so that said outer tube surrounds said inner tube and is spaced therefrom;
    at least one raised lobe extending from an outer surface of said inner tube; and
    at least one diameter restriction on an inner surface of said outer tube in order to engage said raised lobe upon rotation of one of said tubes, wherein said inner tube and said at least one raised lobe allows movement axially with respect to said outer tube during said rotation.

* * * * *